(12) United States Patent
Housmans

(10) Patent No.: US 11,192,834 B2
(45) Date of Patent: Dec. 7, 2021

(54) PROCESS AND SYSTEM FOR PRODUCING PARA-XYLENE

(71) Applicant: SABIC GLOBAL TECHNOLOGIES B.V., Bergen op Zoom (NL)

(72) Inventor: Thomas Hubertus Maria Housmans, Beek (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/254,351

(22) PCT Filed: Jun. 24, 2019

(86) PCT No.: PCT/IB2019/055311
§ 371 (c)(1),
(2) Date: Dec. 21, 2020

(87) PCT Pub. No.: WO2020/003100
PCT Pub. Date: Jan. 2, 2020

(65) Prior Publication Data
US 2021/0323894 A1    Oct. 21, 2021

Related U.S. Application Data

(60) Provisional application No. 62/689,401, filed on Jun. 25, 2018.

(51) Int. Cl.
*C07C 2/64* (2006.01)
*C07C 4/06* (2006.01)
*C07C 7/00* (2006.01)

(52) U.S. Cl.
CPC ............... *C07C 2/64* (2013.01); *C07C 4/06* (2013.01); *C07C 7/005* (2013.01)

(58) Field of Classification Search
CPC ...... C07C 2/66; C07C 15/08; C07C 2/864; C07C 15/06; C07C 15/073; C07C 2/64;
(Continued)

(56) References Cited

U.S. PATENT DOCUMENTS 8,921,633 B2    12/2014  Iaccino et al.
8,937,205 B2 *   1/2015  Iaccino ............... C07C 2/864
                                                585/321
(Continued)

FOREIGN PATENT DOCUMENTS

WO    2013169465 A1    11/2013
WO    2020003100 A1     1/2020

OTHER PUBLICATIONS

International Search Report for International Application No. PCT/IB2019/055311; Application Filing Date: Jun. 24, 2019; dated Oct. 9, 2019, 6 pages.
(Continued)

*Primary Examiner* — Sharon Pregler
(74) *Attorney, Agent, or Firm* — Cantor Colburn LLP

(57) ABSTRACT

A process for producing a para-xylene product from a hydrocarbon feed includes: hydrocracking the hydrocarbon feed in the presence of a catalyst to obtain a hydrocracking product; separating the hydrocracking product to obtain a gas stream and a liquid stream, the liquid stream comprising benzene, toluene, xylene, $C_{9+}$ hydrocarbon, or a combination comprising at least one of the foregoing; separating the liquid stream to obtain a toluene stream, wherein toluene is present in the toluene stream in an amount equal to or greater than 70 wt %, preferably equal to or greater than 80 wt %, more preferably equal to or greater than 95 wt %, based on the total weight of the toluene stream; and reacting the toluene stream with methanol to obtain the para-xylene product.

19 Claims, 1 Drawing Sheet

(58) Field of Classification Search
CPC .............. C07C 2529/08; C07C 2529/16; B01J
2229/183; B01J 29/088; B01J 2229/26;
C10G 2300/1096; C10G 2300/4006;
C10G 2300/4012; C10G 2300/4018;
C10G 2400/30; C10G 11/00; C10G
2300/1048; C10G 2300/1092; C10G
2300/304; C10G 29/20; C10G 29/205;
C10G 35/00; C10G 35/065; C10G 35/24;
C10G 45/64; C10G 57/005; C10G 9/005;
C10G 9/36
See application file for complete search history.

(56) References Cited

U.S. PATENT DOCUMENTS

| | | | |
|---|---|---|---|
| 8,940,950 | B2 | 1/2015 | Ellrich et al. |
| 9,079,816 | B2 | 7/2015 | Johnson et al. |
| 9,249,068 | B2 | 2/2016 | Tinger et al. |
| 2013/0296624 | A1 | 11/2013 | Iaccino et al. |
| 2014/0100398 | A1 | 4/2014 | Jin et al. |
| 2017/0129828 | A1* | 5/2017 | Davies .................... C10G 63/00 |
| 2018/0170831 | A1 | 6/2018 | Jan et al. |

OTHER PUBLICATIONS

Kaeding et al., "Selective Alkylation of Toluene with Methanol to Produce para-Xylene", Journal of Catalysis 67, p. 159-174, 1981.
Written Opinion for International Application No. PCT/IB2019/055311; Application Filing Date: Jun. 24, 2019; dated Oct. 9, 2019, 7 pages.

* cited by examiner

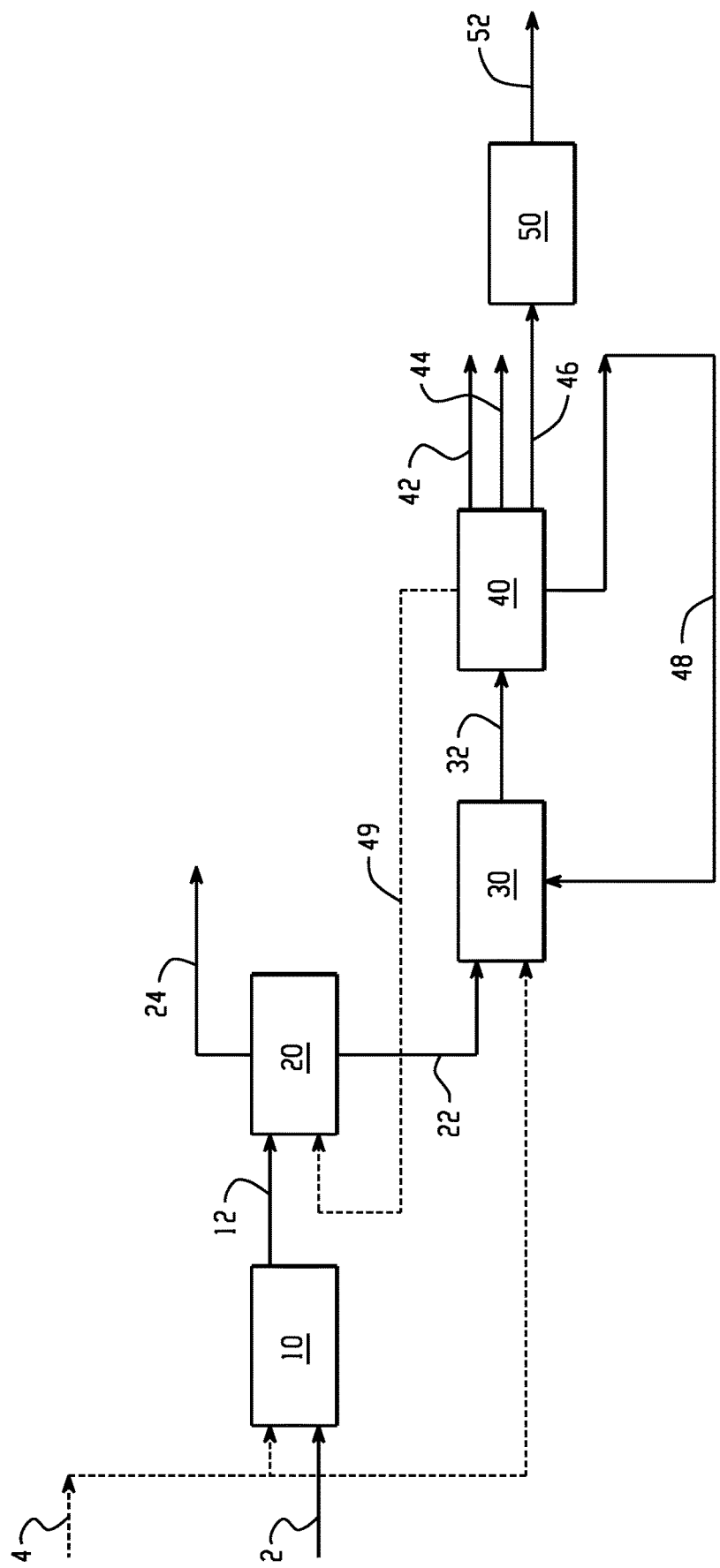

PROCESS AND SYSTEM FOR PRODUCING PARA-XYLENE

CROSS REFERENCE TO RELATED APPLICATIONS

This application is a National Stage application, i.e., a 371 of PCT/IB2019/055311 filed Jun. 24, 2019, which claims the benefit of U.S. Provisional Application No. 62/689,401, filed Jun. 25, 2018, both of which are incorporated by reference in their entirety herein.

BACKGROUND

In the petrochemical industry, hydrocracking can be used to convert highly complex hydrocarbon streams into less complex streams containing fewer components. These less complex streams can include fuel gas (e.g., hydrogen, methane), liquefied petroleum gas (LPG) (e.g., ethane, propane, butane), benzene, toluene, and xylene.

For instance, benzene and xylene products can be produced by hydrocracking hydrocarbon feeds and processing the hydrocracking product with extractive distillation, toluene disproportionation, and selective transalkylation. Alternatively, benzene can be produced by hydrodealkylation of toluene.

Often, benzene is separated from the hydrocracking product to ensure on-specification benzene levels in the production of gasoline. The remaining toluene (which is produced in relatively significant amounts due to thermodynamics) and xylene can be used as a gasoline component due to its high octane value.

SUMMARY

Disclosed, in various embodiments, are processes and systems for producing para-xylene.

A process for producing a para-xylene product from a hydrocarbon feed, comprises: hydrocracking the hydrocarbon feed in the presence of a catalyst to obtain a hydrocracking product; separating the hydrocracking product to obtain a gas stream and a liquid stream, the liquid stream comprising benzene, toluene, xylene, $C_{9+}$ hydrocarbon, or a combination comprising at least one of the foregoing; separating the liquid stream to obtain a toluene stream, wherein toluene is present in the toluene stream in an amount equal to or greater than 70 weight percent (wt %), preferably equal to or greater than 80 wt %, more preferably equal to or greater than 95 wt %, based on the total weight of the toluene stream; and reacting the toluene stream with methanol to obtain the para-xylene product.

A process for producing a para-xylene product from a hydrocarbon feed, comprises: hydrocracking the hydrocarbon feed in the presence of a catalyst to produce a hydrocracking product at a temperature of 300° C. to 580° C., preferably 325° C. to 575° C., more preferably 350° C. to 550° C. and a pressure of 0.3 MegaPascals (MPa) to 5.0 MPa, preferably 0.5 MPa to 4.0 MPa, more preferably 1 MPa to 3 MPa; separating the hydrocracking product to obtain a gas stream and a liquid stream, the liquid stream comprising benzene, toluene, xylene, $C_{9+}$ hydrocarbon, or a combination comprising at least one of the foregoing; separating the liquid stream to obtain a toluene stream, wherein toluene is present in the toluene stream in an amount equal to or greater than 95 wt %, preferably equal to greater than 96 wt %, more preferably equal to or greater than 97 wt %, based on the total weight of the toluene stream; and reacting the toluene stream with methanol to obtain the para-xylene product.

A system for producing a para-xylene product, comprises: a hydrocracking unit for producing a hydrocracking product; a first separation unit for separating the hydrocracking product to obtain a gas stream and a liquid stream; a second separation unit for separating the liquid stream to obtain a toluene stream; and a methylation unit for reacting the toluene stream with methanol to obtain the para-xylene product.

These and other features and characteristics are more particularly described below.

BRIEF DESCRIPTION OF THE DRAWING

The following figure is an exemplary embodiment which is presented for the purposes of illustrating an exemplary embodiment disclosed herein and not for the purposes of limiting the same.

The Figure is an illustration of an embodiment of a process for producing a para-xylene from a hydrocarbon feed.

The above described and other features are exemplified by the following detailed description, examples, and claims.

DETAILED DESCRIPTION

Described herein are processes and systems for producing a para-xylene product from a hydrocarbon feed. In particular, the processes and systems can convert hydrocarbon feeds to the higher value para-xylene product with high selectivity. By-products can be converted or recycled within the processes and systems so that, in addition to the para-xylene product, the product streams include xylene, benzene, and LPG products. Previous processes and systems for producing para-xylene from hydrocarbon feeds (e.g., hydrocracking and/or steam cracking) produced mixtures of aliphatic hydrocarbons and aromatic hydrocarbons that required separation of the aliphatic hydrocarbons from the aromatic components before further processing (e.g., conversion of toluene to para-xylene). Such separation processes, which include extractive distillation, can be capital and energy intensive. Desirably, in some embodiments, the present processes and systems avoid processes such as extractive distillation, as separation of aliphatic hydrocarbons from aromatic hydrocarbons before further processing of the aromatic hydrocarbons is not required.

Moreover, in some embodiments, the present processes and systems avoid processing of toluene via disproportionation or hydrodealkylation, as conversion of toluene to para-xylene is achieved via methylation. By avoiding toluene disproportionation, production of more benzene from toluene through selective toluene disproportionation can be reduced or avoided and the selectivity for para-xylene is increased. By avoiding hydrodealkylation of toluene, the significant amounts of fuel gas produced by such processes are avoided. Thus, the present processes and systems for producing a para-xylene product have simplified logistics, less processing units, and a higher production ratio of para-xylenes to benzene as compared to previous processes for converting hydrocarbon feeds into a para-xylene product. For instance, in a situation where the unit is fed with a reformate stream with the following composition: paraffins 15 wt %; benzene 10 wt %; toluene 30 wt %; ethyl-benzene 5 wt %; xylenes 30 wt %; $C_{9+}$ aromatics 10 wt %, the molar ratio of xylene produced to benzene produced can be equal to or greater than 4:1, for example, 4.75:1 in case all toluene is successfully methylated to xylenes. It is to be noted, that the xylene/benzene ratio depends strongly upon the feedstock. The values listed above are a typical reformate stream as feedstock.

Additionally, the equilibrium of ortho, meta, and para-xylene is typically 22:54:24%. This means that the ratio of para-xylene/benzene depends on whether or not an isomerization unit is used. Assuming this is the case, nearly all mixed xylenes would be converted to para-xylene and thus the ratio would be approximately the same. Further, it is interesting to note that the selectivity of toluene methylation to para-xylene is nearly 100%. Thus, the present process not only eliminates the need of benzene and toluene extraction through extractive distillation, it reduces the size of the required isomerization unit. In contrast, previous processes using toluene disproportionation had a molar ratio of xylene produced to benzene produced about 1.5:1, while other processes using hydrodealkylation of toluene had a molar ratio of xylene produced to benzene produced of about 0.6:1. When full conversion of mixed-xylenes is achieved through an isomerization unit, these ratios can be considered close to the ratio between para-xylene and benzene.

As used herein "para-xylene product" refers to a composition including para-xylene in an amount equal to or greater than 50 wt %, based on the total weight of the para-xylene product. As used herein, "xylene" refers to a mixture of ortho-xylene, meta-xylene, para-xylene, and ethylbenzene, wherein para-xylene is present in an amount less than 50 wt %, based on the total weight of the xylenes.

A process for producing a para-xylene product from a hydrocarbon feed can include hydrocracking the hydrocarbon feed in the presence of a catalyst to obtain a hydrocracking product, separating the hydrocracking product to obtain a gas stream and a liquid stream, the liquid stream comprising benzene, toluene, xylene, $C_{9+}$ hydrocarbon, or a combination comprising at least one of the foregoing, separating the liquid stream to obtain a toluene stream, and reacting the toluene stream with methanol to obtain the para-xylene product. The toluene is present in the toluene stream in an amount equal to or greater than 70 wt %, for example, equal to or greater than 80 wt %, for example, equal to or greater than 95 wt %, based on the total weight of the toluene stream. As referred to herein, "$C_{9+}$ hydrocarbon" refers to a hydrocarbon including nine or more carbon atoms.

Desirable hydrocarbon feeds include, but are not limited to, hydrogenated depentanized hydrotreated gasoline, naphtha (such as straight run naphtha or light coker naphtha), pyrolysis gasoline (e.g., first stage hydro-treated pyrolysis gasoline), hydrocracked gasoline, coke oven light oil, fluid catalytic cracking (FCC) gasoline, reformate, kerosene, $C_5$-$C_{12}$ hydrocarbons, or a combination comprising at least one of the foregoing. Desirably, the hydrocarbon feed can include naphtha. In an embodiment, a majority of the hydrocarbon feed comprises $C_6$-$C_8$ hydrocarbons.

As used herein, "hydrocracking" refers to a catalytic cracking process in the presence of hydrogen. As used herein, "hydrocracking unit" refers to a reactor unit capable of performing a hydrocracking process. A majority of the effluent produced by hydrocracking can be LPG, which includes alkanes that can be converted to olefins. The hydrocracking can keep intact one aromatic ring of the aromatics in the hydrocarbon feed, but remove most of the side-chains from the aromatic ring. The hydrocracking can be achieved by adjusting the hydrogenation activity of the catalyst, process temperature, or space velocity of the hydrocarbon feed.

Desirably, the processes and systems operate one or more hydrocracking units at moderate temperatures and pressures. The process conditions used for hydrocracking can include a temperature of 300° C. to 580° C., for example, 325° C. to 575° C., for example, 350° C. to 550° C. and a pressure of 0.3 MPa to 20.0 MPa, for example, 0.5 MPa to 4.0 MPa, for example, 1 MPa to 3 MPa. A first hydrocracking unit can be operated at a temperature of 300° C. to 500° C., for example, 400° C. to 500° C. and at a pressure of 0.5 MPa to 3.0 MPa, for example, 1.0 MPa to 2.5 MPa. A second hydrocracking unit can be operated at a temperature of 400° C. to 600° C., for example, 450° C. to 550° C. and at a pressure of 0.5 MPa to 3.0 MPa, for example, 1.0 MPa to 2.5 MPa.

Many catalysts used for the hydrocracking process include various transition metals, or metal sulfides with a solid support such as alumina, silica, alumina-silica, magnesia, zeolites, or a combination comprising at least one of the foregoing. In an embodiment, the catalyst can include 0.01 wt % to 1 wt % hydrogenation metal in relation to the total catalyst weight and a zeolite having a pore size of 5 to 8 Angstroms (Å) and a silica ($SiO_2$) to alumina ($Al_2O_3$) molar ratio of 5:1 to 200:1.

In an embodiment, the hydrocracking can be in the presence of one catalyst. In another embodiment, the hydrocracking can be in the presence of two catalysts.

Desirably, the step of hydrocracking the hydrocarbon feed to produce a hydrocracking product can be in one or more stages. For instance, a first stage can include hydrocracking the hydrocarbon feed to obtain a first hydrocracking product and then separating the first hydrocracking product to obtain a light stream, which can be gaseous, and a heavy stream, which can be a liquid. In an embodiment, a single hydrocracking step can be performed in multiple reactors. When greater than one reactor is used, tailoring of the $C_1$-$C_4$ stream can be allowed. For example, by first mild hydrocracking and then more severe hydrocracking, the ethane/propane/(benzene, toluene, xylene) ratio can be tuned. However, a single step can be possible as well.

The light stream separated from the first hydrocracking product can include hydrogen and $C_1$-$C_4$ hydrocarbons. The heavy stream separated from the first hydrocracking product can include $C_{5+}$ hydrocarbons. As refer to herein, "$C_{1-4}$ hydrocarbons" refers to hydrocarbons including 1 to 4 carbon atoms.

Hydrogen can be present in the first hydrocracking product in an amount equal to or greater than 1 wt %, for example, 2 wt % to 10 wt %, for example, 2 wt % to 8 wt %, based on the total weight of the first hydrocracking product. The $C_1$-$C_4$ hydrocarbons (e.g., LPG) can be present in an amount equal to or greater than 30 wt %, for example, equal to or greater than 40 wt %, for example, equal to or greater 50 wt %, based on the total weight of the first hydrocracking product.

The heavy stream can include $C_{5+}$ hydrocarbons and aromatic hydrocarbons. For instance, the heavy stream can include $C_{5+}$ hydrocarbons in an amount equal to or greater than 1 wt %, for example, 2 wt % to 20 wt %, for example, 5 wt % to 10 wt %, based on the total weight of the heavy stream. In certain embodiments, the heavy stream can include aromatic hydrocarbons in an amount equal to or greater than 1 wt %, for example, 5 wt % to 25 wt %, for example, 10 wt % to 20 wt %, based on the total weight of the heavy stream.

A second stage can include hydrocracking the heavy stream to obtain a second hydrocracking product. The second hydrocracking product obtained from hydrocracking the heavy stream can include hydrogen, methane, ethane, propane, butane, benzene, toluene, xylene, $C_{9+}$ hydrocarbon, or a combination comprising at least one of the foregoing.

The second hydrocracking product can be separated to obtain the gas stream and the liquid stream including benzene, toluene, xylene, $C_{9+}$ hydrocarbon, or a combination comprising at least one of the foregoing. The gas stream can include hydrogen, methane, ethane, propane, butane, or a combination comprising at least one of the foregoing.

The hydrocracking product (e.g., the first hydrocracking product or the second hydrocracking product) can include benzene, toluene, and xylene in an amount of 20 wt % to over 90 wt % (and even 100 wt %, in some cases, can be possible provided that the feedstock fed to the hydrocrackers is easily crackable), for example, 30 wt % to 70 wt %, for example, 40 wt % to 60 wt %, based on the total weight of the hydrocracking product. Toluene can be present in the hydrocracking product in an amount of 10 wt % to 70 wt %, for example, 20 wt % to 60 wt %, for example, 30 wt % to 50 wt %, based on the total weight of the hydrocracking product.

The hydrocracking product (e.g., the liquid stream) can be substantially devoid of aliphatic hydrocarbon (i.e., include less than 1 wt %, based on the total weight of the hydrocracking product). For example, the hydrocracking product (e.g., the liquid stream) can be substantially devoid of $C_5$-$C_7$ aliphatic hydrocarbons (i.e., aliphatic hydrocarbons with 5 to 7 carbon atoms).

Separating the hydrocracking product can include distilling the hydrocracking product to obtain the liquid stream.

Desirably, in the process for producing a para-xylene product, the separating of the liquid stream can include distilling the liquid stream.

In addition to using methylation to produce para-xylene product, the process for producing a para-xylene product can further include, before or during the step of separating the liquid stream to obtain the toluene stream, separating a xylene stream from the liquid stream and transalkylating the xylene stream to obtain para-xylene.

The process for producing a para-xylene product can further include, before or during the step of separating the liquid stream to obtain the toluene stream, separating a $C_{9+}$ hydrocarbon stream from the liquid stream. The process for producing a para-xylene product can further include recycling the $C_{9+}$ hydrocarbon stream to the step of hydrocracking (e.g., the first stage, the second stage, or subsequent stages of the step of hydrocracking).

The reacting of the toluene with methanol to obtain para-xylene can be in the presence of a catalyst. Desirable catalysts for toluene methylation include, but are not limited to, an acidic catalyst, preferably a zeolite catalyst. For example, ZSM-5-type zeolite, zeolite Beta and silicaaluminophosphate (SAPO) catalysts have been used for toluene methylation.

The para-xylene can be present in the para-xylene product an amount equal to or greater than 95 wt %, for example, equal to greater than 96 wt %, for example, equal to or greater than 97 wt %, based on the total weight of the para-xylene product.

Desirably, disproportionation, hydrodealkylation, extractive distillation, or a combination of at least one of the foregoing, are not present in the process for producing a para-xylene product.

A process for producing a para-xylene product from a hydrocarbon feed can include: (i) hydrocracking the hydrocarbon feed in the presence of a catalyst to produce a hydrocracking product at a temperature of 300° C. to 580° C., for example, 325° C. to 575° C., for example, 350° C. to 550° C. and a pressure of 0.3 MPa to 5.0 MPa, for example, 0.5 MPa to 4.0 MPa, for example, 1 MPa to 3 MPa, (ii) separating the hydrocracking product to obtain a gas stream and a liquid stream, the liquid stream comprising benzene, toluene, xylene, $C_{9+}$ hydrocarbon, or a combination comprising at least one of the foregoing, (iii) separating the liquid stream to obtain a toluene stream, wherein toluene is present in the toluene stream in an amount equal to or greater than 95 wt %, for example, equal to greater than 96 wt %, for example, equal to or greater than 97 wt % based on the total weight of the toluene stream; and (iv) reacting the toluene stream with methanol to obtain the para-xylene product.

A para-xylene product can be produced by the above-described processes.

A system for producing a para-xylene product can include a hydrocracking unit for producing a hydrocracking product, a first separation unit for separating the hydrocracking product to obtain a gas stream and a liquid stream, a second separation unit for separating the liquid stream to obtain a toluene stream, and a methylation unit for reacting the toluene stream with methanol to obtain the para-xylene product.

A more complete understanding of the components, processes, and apparatuses disclosed herein can be obtained by reference to the accompanying Figure. The Figure is merely a schematic representation based on convenience and the ease of demonstrating the present disclosure, and is, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiment selected for illustration in the drawing, and are not intended to define or limit the scope of the disclosure.

In an exemplary process illustrated in the Figure, a hydrocarbon feed 2 can be hydrocracked over a catalyst in a first hydrocracking unit 10 to produce a first hydrocracking product 12. In the first hydrocracking unit 10, the hydrocarbon feed 2 can be mixed with hydrogen 4 and heated. The first hydrocracking product 12 can comprise hydrogen, $C_1$-$C_4$ hydrocarbons (such as liquefied petroleum gas), and $C_{5+}$ hydrocarbons (i.e., those comprising five or more carbon atoms), including aromatic hydrocarbons such as benzene, toluene, and xylene (BTX).

After partial cooling, the first hydrocracking product 12 enters a first separation unit 20. The first separation unit 20 separates hydrogen and $C_1$-$C_4$ hydrocarbons from $C_{5+}$ hydrocarbons to obtain a light stream 24 and a heavy stream 22, respectively.

The heavy stream 22 is hydrocracked in a second hydrocracking unit 30 to convert at least a portion of the $C_{5+}$ hydrocarbons into $C_1$-$C_4$ hydrocarbons and aromatic hydrocarbons. In some embodiments, conversion of at least a portion of the $C_{5+}$ hydrocarbons into $C_1$-$C_4$ hydrocarbons and aromatic hydrocarbons can be achieved in the second hydrocracking unit 30 without the use of paraffinic and naphthenic co-boilers, which can affect the purity of the aromatic products. In the second hydrocracking unit 30, the heavy stream 22 and hydrogen 4 react over a catalyst to produce a second hydrocracking product 32.

Although the first hydrocracking unit 10 and the second hydrocracking unit 30 are each shown as one single unit, it is to be understood that in alternate embodiments the hydrocracking units comprise multiple reactors. For instance, a hydrocracking unit can comprise one, two, three, four, or more fixed-bed reactors or one, two, three, four, or more fluidized bed reactors in series, each comprising a catalyst. Optionally, intermediate coolers can be located among the reactors to remove the heat of the reaction by, for instance, producing high pressure steam.

A second separation unit 40 removes hydrogen and light hydrocarbons (e.g., $C_5$-hydrocarbons) in the second hydrocracking product 32 from aromatic hydrocarbons. Hydrogen and light hydrocarbons in a gas stream 49 are directed to the first separation unit 20, while aromatic hydrocarbons enter a distillation train where sequential separation of benzene 42, $C_8$ hydrocarbons 44, toluene 46, and $C_{9+}$ hydrocarbons 48 occurs.

Although the second separation unit 40 is shown as one single unit, it is to be understood that in alternate embodiment's second separation comprise multiple distillation columns making up the distillation train. For instance, a hydrocracking unit can comprise one, two, three, four, or more simple distillation columns in series.

The toluene 46 is fed to a reactor 50 and reacted with methanol to obtain a para-xylene product 52.

The $C_{9+}$ hydrocarbons 48 can be recycled to the hydrocracking unit 30.

This disclosure is further illustrated by the following example, which is non-limiting.

Example

A process for producing para-xylene from a hydrocarbon feed was performed with hydrogenated depentanized hydrotreated gasoline using the process illustrated in the Figure. Table 1 shows the $C_7$ fraction from a run using the hydrogenated depentanized hydrotreated gasoline (HPHG) with mild hydrocracking (MHC). Operating conditions for the mild hydrocracking were a temperature of 425 to 475° C. and a pressure of 13 to 15 barg (13.1 MPa to 15.1 MPa).

TABLE 1

$C_7$ Fraction Components using Hydrogenated DPHG with MHC

| Component | Amount (wt %) |
| --- | --- |
| trans 1,3-dimethyl 4-chlorophenyl thiophosphate | 0.01 |
| 1,3-dimethyl 4-chlorophenyl thiophosphate | 0.02 |
| 1,2-dimethyl 4-chlorophenyl thiophosphate | 0.00 |
| 2,2,4-trimethylpentane | 0.04 |
| heptane | 0.01 |
| methylcyclohexane | 0.00 |
| toluene | 17.55 |

After the mild hydrocracking, the benzene purity was 99.88 wt %, based on the total weight of the benzene stream, while the toluene purity was 99.5 wt %, based on the total weight of the toluene stream. In the step of reacting toluene with methanol, the toluene conversion was 41.7%, the toluene selectivity to the para-xylene product was 93.1%, and para-xylene was present in the para-xylene product in an amount of 83.3 weight %, based on the total weight of the para-xylene product. Methanol and toluene can be recycled to maximize conversion. Heavies (e.g., greater than $C_{9+}$) can be recycled in the hydrocracking unit or can be sold.

Thus, in some embodiments, the processes and systems of the present disclosure achieved higher yields of para-xylene from a hydrocarbon feedstock, such as naphtha, while reducing the capital and energy expenditure. In contrast, conventional processes use greater capital and energy expenditure because they use extractive distillation to separate aliphatic hydrocarbons from aromatic hydrocarbons before further processing of aromatic hydrocarbons. Conventional processes require the combined use of hydrogenation, distillation, and extractive distillation to produce the desired product, while the use of hydrocracking in the present process generally removes all aliphatic components from aromatics by conversion to gas which is easily separated. The remaining aromatics have few to no co-boilers and can be further separated with simple distillation. In addition, in some embodiments, the processes and systems of the present disclosure produce a higher molar ratio of para-xylene to benzene.

The processes and system disclosed herein include(s) at least the following aspects:

Aspect 1: A process for producing a para-xylene product from a hydrocarbon feed, comprising: hydrocracking the hydrocarbon feed in the presence of a catalyst to obtain a hydrocracking product; separating the hydrocracking product to obtain a gas stream and a liquid stream, the liquid stream comprising benzene, toluene, xylene, $C_{9+}$ hydrocarbon, or a combination comprising at least one of the foregoing; separating the liquid stream to obtain a toluene stream, wherein toluene is present in the toluene stream in an amount equal to or greater than 70 wt %, preferably equal to or greater than 80 wt %, more preferably equal to or greater than 95 wt %, based on the total weight of the toluene stream; and reacting the toluene stream with methanol to obtain the para-xylene product.

Aspect 2: The process of Aspect 1, wherein the hydrocarbon feed comprises hydrogenated depentanized hydrotreated gasoline, naphtha, pyrolysis gasoline, hydrocracked gasoline, coke oven light oil, fluid catalytic cracking gasoline, reformate, kerosene, $C_5$-$C_{12}$ hydrocarbons, or a combination comprising at least one of the foregoing.

Aspect 3: The process of any one or more of the preceding aspects, wherein the hydrocracking is in the presence of one catalyst.

Aspect 4: The process of any one or more of the preceding aspects, wherein the hydrocracking product is substantially devoid of aliphatic hydrocarbons.

Aspect 5: The process of any one or more of the preceding aspects, wherein separating the hydrocracking product comprises distilling the hydrocracking product to obtain the liquid stream.

Aspect 6: The process of any one or more of the preceding aspects, wherein the gas stream comprises hydrogen, methane, ethane, propane, butane, or a combination comprising at least one of the foregoing.

Aspect 7: The process of any one or more of the preceding aspects, wherein separating the liquid stream comprises distilling the liquid stream.

Aspect 8: The process of any one or more of the preceding aspects, further comprising, before or during the step of separating the liquid stream to obtain the toluene stream, separating a xylene stream from the liquid stream and transalkylating the xylene stream to obtain para-xylene.

Aspect 9: The process of any one or more of the preceding aspects, further comprising, before or during the step of separating the liquid stream to obtain the toluene stream, separating a $C_{9+}$ hydrocarbon stream from the liquid stream.

Aspect 10: The process of Aspect 8, further comprising recycling the $C_{9+}$ hydrocarbon stream to the step of hydrocracking.

Aspect 11: The process of any one or more of the preceding aspects, wherein the para-xylene is present in the para-xylene product an amount equal to or greater than 95 wt %, preferably equal to greater than 96 wt %, more preferably equal to or greater than 97 wt %, based on the total weight of the para-xylene product.

Aspect 12: The process of any one or more of the preceding aspects, wherein disproportionation, hydrodealkylation, extractive distillation, or a combination of at least one of the foregoing, are not present in the process.

Aspect 13: The process of any one or more of the preceding aspects, wherein the liquid stream comprises less than 1 wt % of $C_5$-$C_7$ aliphatic hydrocarbons.

Aspect 14: The process of any one or more of the preceding aspects, wherein the liquid stream comprises less than 1 wt % aliphatic hydrocarbon, based on the total weight of the liquid stream.

Aspect 15: The process of any one or more of the preceding aspects, without processing of the toluene via disproportionation or hydrodealkylation.

Aspect 16: The process of any one or more of the preceding aspects, wherein the hydrocracking was at a temperature of 300° C. to 580° C., preferably 325° C. to 575° C., more preferably 350° C. to 550° C. and a pressure of 0.3 MPa to 5.0 MPa, preferably 0.5 MPa to 4.0 MPa, more preferably 1 MPa to 3 MPa;

Aspect 17: A process for producing a para-xylene product from a hydrocarbon feed, comprising: hydrocracking the hydrocarbon feed in the presence of a catalyst to produce a hydrocracking product at a temperature of 300° C. to 580° C., preferably 325° C. to 575° C., more preferably 350° C. to 550° C. and a pressure of 0.3 MPa to 5.0 MPa, preferably 0.5 MPa to 4.0 MPa, more preferably 1 MPa to 3 MPa; separating the hydrocracking product to obtain a gas stream and a liquid stream, the liquid stream comprising benzene, toluene, xylene, $C_{9+}$ hydrocarbon, or a combination comprising at least one of the foregoing; separating the liquid stream to obtain a toluene stream, wherein toluene is present in the toluene stream in an amount equal to or greater than 95 wt %, preferably equal to greater than 96 wt %, more preferably equal to or greater than 97 wt % based on the total weight of the toluene stream; and reacting the toluene stream with methanol to obtain the para-xylene product.

Aspect 18: A para-xylene product produced by the process of any one or more of the preceding aspects.

Aspect 19: A system for producing a para-xylene product, comprising: a hydrocracking unit for producing a hydrocracking product; a first separation unit for separating the hydrocracking product to obtain a gas stream and a liquid stream; a second separation unit for separating the liquid stream to obtain a toluene stream; and a methylation unit for reacting the toluene stream with methanol to obtain the para-xylene product.

Aspect 20: The system of claim 19, wherein no disproportionation unit or hydrodealkylation unit is present between the hydrocracking unit and the methylation unit.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process for producing para-xylene product from a hydrocarbon feed, comprising:
   hydrocracking the hydrocarbon feed in the presence of a catalyst to obtain a hydrocracking product comprising less than 1 weight percent aliphatic hydrocarbons, based on a total weight of the hydrocracking product;
   separating the hydrocracking product to obtain a gas stream and a liquid stream, the liquid stream comprising benzene, toluene, xylene, $C_{9+}$ hydrocarbons, or a combination comprising at least one of the foregoing;
   separating the liquid stream to obtain a toluene stream, wherein toluene is present in the toluene stream in an amount equal to or greater than 70 wt %, based on the total weight of the toluene stream; and reacting the toluene stream with methanol to obtain the para-xylene product.

2. The process of claim 1, wherein the hydrocarbon feed comprises hydrogenated depentanized hydrotreated gasoline, naphtha, pyrolysis gasoline, hydrocracked gasoline, coke oven light oil, fluid catalytic cracking gasoline, reformate, kerosene, $C_5$-$C_{12}$ hydrocarbons, or a combination comprising at least one of the foregoing.

3. The process of claim 1, wherein the hydrocracking is in the presence of one catalyst.

4. The process of claim 1, wherein separating the hydrocracking product comprises distilling the hydrocracking product to obtain the liquid stream.

5. The process of claim 1, wherein the gas stream comprises hydrogen, methane, ethane, propane, butane, or a combination comprising at least one of the foregoing.

6. The process of claim 1, wherein separating the liquid stream comprises distilling the liquid stream.

7. The process of claim 1, further comprising, before or during the step of separating the liquid stream to obtain the toluene stream, separating a xylene stream from the liquid stream and transalkylating the xylene stream to obtain para-xylene.

8. The process of claim 1, further comprising, before or during the step of separating the liquid stream to obtain the toluene stream, separating a $C_{9+}$ hydrocarbon stream from the liquid stream.

9. The process of claim 7, further comprising recycling the $C_{9+}$ hydrocarbon stream to the step of hydrocracking.

10. The process of claim 1, wherein the para-xylene is present in the para-xylene product an amount equal to or greater than 95 wt %, based on the total weight of the para-xylene product.

11. The process of claim 1, wherein disproportionation, hydrodealkylation, extractive distillation, or a combination of at least one of the foregoing, are not present in the process.

12. The process of claim 1, wherein the liquid stream comprises less than 1 wt % of C5-C7 aliphatic hydrocarbons, based on the total weight of the liquid stream.

13. The process of claim 1, wherein the liquid stream comprises less than 1 wt % aliphatic hydrocarbons, based on the total weight of the liquid stream.

14. The process of claim 1, without processing of the toluene via disproportionation or hydrodealkylation.

15. The process of claim 1, wherein the hydrocracking was at a temperature of 300° C. to 580° C., and a pressure of 0.3 MPa to 5.0 MPa.

16. A para-xylene product produced by the process of claim 1.

17. A system for producing a para-xylene product, comprising:

a hydrocracking unit for producing a hydrocracking product;

a first separation unit for separating the hydrocracking product to obtain a gas stream and a liquid stream;

a second separation unit for separating the liquid stream to obtain a toluene stream; and a methylation unit for reacting the toluene stream with methanol to obtain the para-xylene product, wherein no unit for separation of aliphatic hydrocarbons from aromatic hydrocarbons is present.

18. The system of claim 17, wherein no disproportionation unit or hydrodealkylation unit is present between the hydrocracking unit and the methylation unit.

19. The process of claim 1, wherein separation of aliphatic hydrocarbons from aromatic hydrocarbons is not present in the process.

* * * * *